(12) United States Patent
Gerace et al.

(10) Patent No.: US 7,541,418 B2
(45) Date of Patent: Jun. 2, 2009

(54) TRANSPARENT THERMOPLASTIC ANTIMICROBIAL MOLDING COMPOSITION

(75) Inventors: Michael A. Gerace, Slovan, PA (US); James P. Mason, Carnegie, PA (US); John J. Charles, Upper St. Clair, PA (US)

(73) Assignee: Bayer MaterialScience LLC, Pittsburgh, PA (US)

( * ) Notice: Subject to any disclaimer, the term of this patent is extended or adjusted under 35 U.S.C. 154(b) by 245 days.

(21) Appl. No.: 11/318,961

(22) Filed: Dec. 27, 2005

(65) Prior Publication Data

US 2007/0148257 A1 Jun. 28, 2007

(51) Int. Cl.
C08G 64/00 (2006.01)
B32B 9/04 (2006.01)

(52) U.S. Cl. ............... 528/196; 106/39.25; 106/38.35; 106/38.51; 264/219; 264/255; 428/411.1; 428/412; 524/315; 525/64; 525/68; 525/69; 528/198

(58) Field of Classification Search ............. 106/38.25, 106/38.35, 38.51; 264/219, 255; 428/411.1, 428/412; 524/315; 525/64, 68, 69; 528/196, 528/198
See application file for complete search history.

(56) References Cited

U.S. PATENT DOCUMENTS 4,938,955 A 7/1990 Niira et al. ................ 424/79
5,698,212 A 12/1997 Hagiwara ................ 424/409
5,698,229 A 12/1997 Ohsumi et al. ............ 424/604
5,827,524 A 10/1998 Hagiwara et al. .......... 424/409

FOREIGN PATENT DOCUMENTS

JP 07-324225 * 12/1995
JP 10221177 * 8/1998

OTHER PUBLICATIONS

Database WPI Week 200007 Derwent Publications Ltd., London, GB; AN 2000-075769 XP002434272 & JP 11 323117 A (Teijin Kasei Ltd) Nov. 26, 1999 abstract.
Database WPI Week 199844 Derwent Publications Ltd., London, GB; AN 1998-510257 XP002434273 & JP 10 221177 A (Terumo Corp) Aug. 21, 1998 abstract.

* cited by examiner

*Primary Examiner*—Terressa M Boykin
(74) *Attorney, Agent, or Firm*—Noland J. Cheung; John E. Mrozinski, Jr.

(57) ABSTRACT

A transparent antimicrobial thermoplastic molding composition is disclosed. The composition contains aromatic polycarbonate resin and 0.01 to 3.8 of an antimicrobial compound conforming to formula (I)

$$Ag_a M^1{}_b M^2{}_2 (PO_4)_3 \qquad (I)$$

wherein $M^1$ is at least one ion selected from the group consisting of alkali metal ion, alkaline earth metal ion, ammonium ion and hydrogen ion, $M^2$ a tetravalent metal selected from the group consisting of Ti, Zr and Sn, and where a and b are positive numbers where $a+mb=1$ where m is a valence of $M^1$, the percent being relative to the weight of the polycarbonate. The composition is suitable for molding articles having good appearance and surface qualities.

10 Claims, No Drawings

TRANSPARENT THERMOPLASTIC ANTIMICROBIAL MOLDING COMPOSITION

FIELD OF THE INVENTION

The invention relates to a thermoplastic, transparent molding composition and in particular to an antimicrobial composition.

BACKGROUND OF THE INVENTION

Inorganic, silver containing antimicrobial compounds are known. Relevant disclosures were made in U.S. Pat. No. 4,938,955 that disclosed an antibiotic resin composition containing antibiotic zeolite. U.S. Pat. No. 5,698,212 disclosed an antimicrobial polymer composition containing a polymer and an antimicrobial coat of an aluminosilicate on the surface of silica gel. U.S. Pat. No. 5,698,229 disclosed an antimicrobial composition that contains a presently relevant inorganic compound and a benzotriazole as a discoloration inhibitor. The antimicrobial polymer composition disclosed in U.S. Pat. No. 5,827,524 included a crystalline silicon dioxide containing silver ions and one or two optional metal ions selected from the group consisting of zinc and copper as antimicrobial composition.

SUMMARY OF THE INVENTION

A transparent antimicrobial thermoplastic molding composition is disclosed. The composition contains aromatic polycarbonate resin and 0.01 to 3.8 of an antimicrobial compound conforming to formula (I)

$$Ag_aM^1{}_bM^2{}_2(PO_4)_3 \qquad (I)$$

wherein $M^1$ is at least one ion selected from the group consisting of alkali metal ion, alkaline earth metal ion, ammonium ion and hydrogen ion, $M^2$ a tetravalent metal selected from the group consisting of Ti, Zr and Sn, and where a and b are positive numbers where a+mb=1 where m is a valence of $M^1$, the percent being relative to the weight of the polycarbonate. The composition is suitable for molding articles having good appearance and surface qualities.

DETAILED DESCRIPTION OF THE INVENTION

The inventive transparent thermoplastic composition contains aromatic polycarbonate resin and 0.01 to 3.8, preferably 0.1 to 3.5 more preferably 0.3 to 2.5 percent (the percent relative to the weight of the polycarbonate) of an antimicrobial compound.

Polycarbonate suitable in the present context include homopolycarbonates, copolycarbonates and polyestercarbonates (the term polycarbonate as used herein refers to any of these resins) and mixtures thereof.

Polycarbonates are known and their structure and methods of preparation have been disclosed, for example, in U.S. Pat. Nos. 3,030,331; 3,169,121; 3,395,119; 3,729,447; 4,255,556; 4,260,731; 4,369,303, 4,714,746 and 6,306,507 all of which are incorporated by reference herein. The polycarbonates generally have a weight average molecular weight of 10,000 to 200,000, preferably 20,000 to 80,000 and their melt flow rate, per ASTM D-1238 at 300° C., under 1.2 Kg load, is about 1 to about 65 g/10 min., preferably about 2 to 35 g/10 min. They may be prepared, for example, by the known diphasic interface process from a carbonic acid derivative such as phosgene and dihydroxy compounds by polycondensation (see German Offenlegungsschriften 2,063,050; 2,063,052; 1,570,703; 2,211,956; 2,211,957 and 2,248,817; French Patent 1,561,518; and the monograph by H. Schnell, "Chemistry and Physics of Polycarbonates", Interscience Publishers, New York, N.Y., 1964, all incorporated herein by reference).

In the present context, dihydroxy compounds suitable for the preparation of the polycarbonates of the invention conform to the structural formulae (1) or (2).

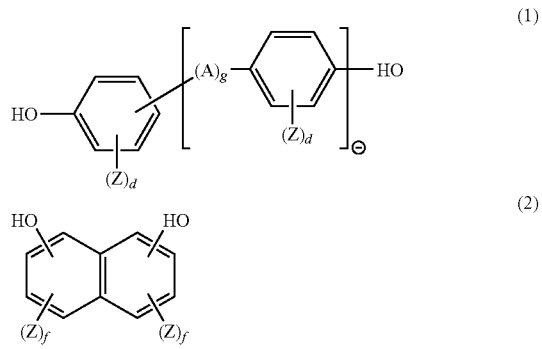

wherein

A denotes an alkylene group with 1 to 8 carbon atoms, an alkylidene group with 2 to 8 carbon atoms, a cycloalkylene group with 5 to 15 carbon atoms, a cycloalkylidene group with 5 to 15 carbon atoms, a carbonyl group, an oxygen atom, a sulfur atom, —SO— or —SO$_2$ or a radical conforming to

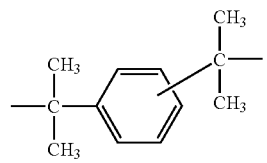

e and g both denote the number 0 to 1;

Z denotes F, Cl, Br or $C_1$-$C_4$-alkyl and if several Z radicals are substituents in one aryl radical, they may be identical or different from one another;

d denotes an integer of from 0 to 4; and f denotes an integer of from 0 to 3.

Among the dihydroxy compounds useful in the practice of the invention are hydroquinone, resorcinol, bis-(hydroxyphenyl)-alkanes, bis-(hydroxyphenyl)-ethers, bis-(hydroxyphenyl)-ketones, bis-(hydroxy-phenyl)-sulfoxides, bis-(hydroxyphenyl)-sulfides, bis-(hydroxyphenyl)-sulfones, and α,α-bis-(hydroxyphenyl)-diisopropylbenzenes, as well as their nuclear-alkylated compounds. These and further suitable aromatic dihydroxy compounds are described, for example, in U.S. Pat. Nos. 5,105,004; 5,126,428; 5,109,076; 5,104,723; 5,086,157; 3,028,356; 2,999,835; 3,148,172; 2,991,273; 3,271,367; and 2,999,846, all incorporated herein by reference.

Further examples of suitable bisphenols are 2,2-bis-(4-hydroxy-phenyl)-propane (bisphenol A), 2,4-bis-(4-hydroxyphenyl)-2-methyl-butane, 1,1-bis-(4-hydroxyphenyl)-cyclohexane, α,α'-bis-(4-hydroxy-phenyl)-p-diisopropylbenzene, 2,2-bis-(3-methyl-4-hydroxyphenyl)-propane, 2,2-bis-(3-chloro-4-hydroxyphenyl)-propane, bis-(3,5-dimethyl-4-hydroxyphenyl)-methane, 2,2-bis-(3,5-dimethyl-4-hydroxyphenyl)-propane, bis-(3,5-dimethyl-4- hydroxyphenyl)-sulfide, bis-(3,5-dimethyl-4-hydroxy-phenyl)-sulfoxide, bis-(3,5-dimethyl-4-hydroxyphenyl)-sulfone, dihydroxy-benzophenone, 2,4-bis-(3,5-dimethyl-4-hydroxyphenyl)-cyclohexane, α,α'-bis-(3,5-dimethyl-4-hydroxyphenyl)-p-diisopropyl-benzene and 4,4'-sulfonyl diphenol.

Examples of particularly preferred aromatic bisphenols are 2,2-bis-(4-hydroxyphenyl)-propane, 2,2-bis-(3,5-dimethyl-4-hydroxyphenyl)-propane, 1,1-bis-(4-hydroxyphenyl)-cyclohexane and 1,1-bis-(4-hydroxy-phenyl)-3,3,5-trimethyl-cyclohexane.

The most preferred bisphenol is 2,2-bis-(4-hydroxyphenyl)-propane (bisphenol A).

The polycarbonates of the invention may entail in their structure units derived from one or more of the suitable bisphenols.

Among the resins suitable in the practice of the invention are polyestercarbonate based on resorcinol and bisphenol A (registry number 265997-77-1), phenolphthalein-based polycarbonate, copolycarbonates and terpoly-carbonates such as are described in U.S. Pat. Nos. 6,306,507, 3,036,036 and 4,210,741, all incorporated by reference herein.

The polycarbonates of the invention may also be branched by condensing therein small quantities, e.g., 0.05 to 2.0 mol % (relative to the bisphenols) of polyhydroxyl compounds.

Polycarbonates of this type have been described, for example, in German Offenlegungsschriften 1,570,533; 2,116,974 and 2,113,374; British Patents 885,442 and 1,079,821 and U.S. Pat. No. 3,544,514. The following are some examples of polyhydroxyl compounds which may be used for this purpose: phloroglucinol; 4,6-dimethyl-2,4,6-tri-(4-hydroxy-phenyl)-heptane; 1,3,5-tri-(4-hydroxyphenyl)-benzene; 1,1,1-tri-(4-hydroxyphenyl)-ethane; tri-(4-hydroxyphenyl)-phenylmethane; 2,2-bis-[4,4-(4,4'-dihydroxydiphenyl)]-cyclohexyl-propane; 2,4-bis-(4-hydroxy-1-isopropylidine)-phenol; 2,6-bis-(2'-dihydroxy-5'-methylbenzyl)-4-methyl-phenol; 2,4-dihydroxybenzoic acid; 2-(4-hydroxyphenyl)-2-(2,4-dihydroxy-phenyl)-propane and 1,4-bis-(4,4'-dihydroxytriphenylmethyl)-benzene. Some of the other polyfunctional compounds are 2,4-dihydroxy-benzoic acid, trimesic acid, cyanuric chloride and 3,3-bis-(4-hydroxyphenyl)-2-oxo-2,3-dihydroindole.

In addition to the polycondensation process mentioned above, other processes for the preparation of the polycarbonates of the invention are polycondensation in a homogeneous phase and transesterification. The suitable processes are disclosed in the incorporated herein by reference, U.S. Pat. Nos. 3,028,365; 2,999,846; 3,153,008; and 2,991,273.

The preferred process for the preparation of polycarbonates is the interfacial polycondensation process. Other methods of synthesis in forming the polycarbonates of the invention, such as disclosed in U.S. Pat. No. 3,912,688, incorporated herein by reference, may be used.

Suitable polycarbonate resins are available in commerce, for instance, from Bayer MaterialScience LLC under the Makrolon trademark.

The antimicrobial agent entailed in the inventive composition conforms to formula (I)

$$Ag_a M^1{}_b M^2{}_2 (PO_4)_3 \quad (I)$$

wherein
M$^1$ is at least one ion selected from the group consisting of alkali metal ion, alkaline earth metal ion, ammonium ion and hydrogen ion,
M$^2$ a tetravalent metal selected from the group consisting of Ti, Zr and Sn, preferably Zr, and a and b are positive numbers where a+mb=1 where m is a valence of M$^1$.

Examples of the suitable phosphates include:

$$Ag_{0.005}Li_{0.995}Zr_2(PO_4)_3$$

$$Ag_{0.01}(NH_4)_{0.99}Zr_2(PO_4)_3$$

$$Ag_{0.05}Na_{0.95}Zr_2(PO_4)_3$$

$$Ag_{0.2}K_{0.8}Ti_2(PO_4)_3$$

$$Ag_{0.1}H_{0.9}Zr_2(PO_4)_3$$

$$Ag_{0.05}H_{0.05}Na_{0.90}Zr_2(PO_4)_3$$

$$Ag_{0.05}H_{0.55}Na_{0.40}Zr_2(PO_4)_3$$

Especially suitable is a compound conforming to $$Na_x H_y Ag_z Zr_2(PO_4)_3$$

where x+y+z=1.

A suitable phosphate may be prepared as follows:

Oxalic acid is added to an aqueous solution of zirconium oxynitrate and sodium nitrate with stirring and then phosphoric acid is added. The pH of the reaction mixture is adjusted to 3.5 with an aqueous sodium hydroxide solution and refluxed with heating for 78 hours. The precipitate is filtered, washed with water, dried and ground to obtain zirconium phosphate that is then immersed in an aqueous solution containing silver ion at a suitable concentration to obtain the compound represented by formula 1.

Suitable commercial antimicrobial agents are available from Milliken Chemical Co. as Alphasan RC 5000 and Alphasan RC 2000. The bound water in hydrated forms of the antimicrobial agent e.g. $Ag_a M^1{}_b M^2{}_2 (PO_4)_3 \cdot nH_2O$ (where n is a positive number up to 6) are driven off in the course of compounding and/or thermoplastic processing.

The inventive composition may contain additional functional components including such as mold release agents, colorants, hydrolytic stabilizers, radiation stabilizers, UV absorbers, antioxidants, surfactants, foaming agents, fillers, extenders, flame retardants and reinforcing agents. Additionally optionally included are other resins provided their inclusion does not degrade the transparency of the inventive composition—these include one or more of thermoplastic polyesters (e.g. PET, PBT, PCTG, PCT, PETG, and PTT) and vinyl polymers (e.g. PMMA, SAN, ABS, EPDM, MBS, Poly butyl acrylate)

In the preferred embodiments the inventive compositions contain no benzotriazoles.

Thermoplastic compositions that contain the antimicrobial agent and are translucent or opaque are not within the scope of the invention.

The antimicrobial composition of the present invention is prepared by mixing the antimicrobial agent with or without the conventional additives noted above in the polycarbonate resin. The procedure and apparatus for making the composition are conventional and are well known in the art.

The composition of the present invention may be used in preparing useful articles by any method of thermoplastic processing including injection molding and extrusion.

The invention is explained in more detail by the following examples.

In preparing the exemplified composition the polycarbonate used was a bisphenol-A based homopolycarbonate resin, Makrolon 2458 polycarbonate a product of Bayer MaterialScience LLC, characterized in that its melt flow index per ASTM D 1238 is 20 g/10 min.

The exemplified compositions contained the indicated amount and type of antimicrobial compound.

The antimicrobial compounds used in the experiments were:

Antimicrobial compound 1 (AM1): soluble glass containing silver—Inopure IZA, a product of Izhizuka Glass Ltd.

Antimicrobial compound 2 (AM2): soluble glass containing silver—Inopure IPL, a product of Izhizuka Glass Ltd.

Antimicrobial compound 3 (AM3): zeolite containing silver—Agion AJ, a product of Agion.

Antimicrobial compound 4 (AM4): zeolite containing silver—Agion XAJ, a product of Agion.

Antimicrobial compound 5 (AM5): ceramic containing silver—Sanitized BC A 21-61, a product of Sanitized AG.

Antimicrobial compound 6 (AM6): Alphasan RC 2000.

The table below describes the makeup and relevant properties of the exemplified compositions:

|  | 1 | 2 | 3 | 4 | 5 | 6 | 7 | 8 | 9 | 10 | 11 | 12[c] |
|---|---|---|---|---|---|---|---|---|---|---|---|---|
| AM1, wt % | 1 | – | – | – | – | – | – | – | – | – | – | – |
| AM2, wt % | – | 1 | – | – | – | – | – | – | – | – | – | – |
| AM3, wt % | – | – | 1 | – | – | – | – | – | – | – | – | – |
| AM4, wt % | – | – | – | 1 | – | – | – | – | – | – | – | – |
| AM5, wt % | – | – | – | – | 0.3 | – | – | – | – | – | – | – |
| AM6, wt % | – | – | – | – | – | 0.3 | 0.5 | 1 | 2 | 4 | 8 | – |
| Properties |  |  |  |  |  |  |  |  |  |  |  |  |
| 20° gloss | 75 | 63 | 65 | 88 | 92 | 118 | 110 | 91 | 76 | 66 | 48 | 172 |
| Surface appearance[2] | P | P | S | S | P | S | S | S | S | S | S | S |
| Transparency[3] | C | C | O | O | C | C | C | C | C | T | O | C |
| Resolution scale[1] | 316 | 100 | n/a | n/a | 316 | 316 | 316 | 300 | 211 | 100 | n/a | 316 |
| Resolution[4] | + | 0 | – | – | + | + | + | + | + | 0 | – | + |
| Gloss[5] | 0 | – | – | + | + | ++ | ++ | + | 0 | – | –– | ++ |
| Pitting[6] | – | – | 0 | 0 | – | 0 | 0 | 0 | 0 | 0 | 0 | 0 |

[c] control
[1] Resolution is measured using a chart that includes closely spaced lines with light spaces between them. The more lines that can be distinguished in a given area, the better the resolution. In the present context, a flat test specimen 0.1" thick made of the composition to be evaluated, is positioned 0.1" above the surface of the chart and the number of lines per inch that can be resolved in a measure of resolution. Resolution chart comply with ISO 12233 standard.
[2] P denotes pitted surface; S denotes a smooth surface.
[3] C = clear; O = opaque; T = translucent.
[4] Resolution: "+" means greater than 211 lines/inch; "0" means 35 to 211 lines/inch; "–" means less than 35 lines/inch.
[5] The gloss ratings – determined in accordance with ASTM D 2457 - are as follows: "0" means 70-79; "+" means 80-99; "++" means greater than 100; "–" means 60-69; and "––" means less than 60.
[6] The pitting ratings determined by observation are as follows: "0" means no pitting; "–" means pitted.

The results show the inventive antimicrobial composition to exhibit better gloss, surface appearance and surface quality than corresponding compositions differing only in terms of their respective antimicrobial compounds.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A transparent thermoplastic molding composition comprising aromatic polycarbonate resin and 0.01 to 3.8 weight percent of an antimicrobial compound conforming to formula (I)

$$Ag_a M^1_b M^2_2 (PO_4)_3 \qquad (I)$$

wherein $M^1$ is at least one ion selected from the group consisting of alkali metal ion, alkaline earth metal ion and ammonium ion, $M^2$ is a tetravalent metal selected from the group consisting of Ti, Zr and Sn, a and b are positive numbers and $a+mb=1$ where m is a valence of $M^1$, the percent being relative to the weight of the polycarbonate.

2. The composition of claim 1 wherein the antimicrobial compound is present in an amount of 0.1 to 3.5 weight percent.

3. The composition of claim 1 wherein the antimicrobial compound is a member selected from the group consisting of $Ag_{0.005} Li_{0.995} Zr_2(PO_4)_3$; $Ag_{0.01}(NH_4)_{0.99} Zr_2(PO_4)_3$; $Ag_{0.05} Na_{0.95} Zr_2(PO_4)_3$; $Ag_{0.2} K_{0.8} Ti_2(PO_4)_3$; $Ag_{0.05} H_{0.05} Na_{0.90} Zr_2(PO_4)_3$; and $Ag_{0.05} H_{0.55} Na_{0.40} Zr_2(PO_4)_3$.

4. The composition of claim 1 wherein antimicrobial compound conforms to $$Na_x H_y Ag_z Zr_2(PO_4)_3$$

where $x+y+z=1$.

5. An article of manufacture comprising the composition of claim 1.

6. A transparent thermoplastic molding composition comprising aromatic polycarbonate resin and 0.1 to 3.5 weight percent of an antimicrobial compound conforming to formula (I)

$$Ag_a M^1_b M^2_2 (PO_4)_3 \qquad (I)$$

wherein $M^1$ is at least one ion selected from the group consisting of alkali metal ion, alkaline earth metal ion and ammonium ion, $M^2$ is a tetravalent metal selected from the group consisting of Ti, Zr and Sn, a and b are positive numbers and $a+mb=1$ where m is a valence of $M^1$, the percent being relative to the weight of the polycarbonate, said composition including no benzotriazole.

7. The composition of claim 6 wherein the antimicrobial compound is a member selected from the group consisting of $Ag_{0.005}Li_{0.995}Zr_2(PO_4)_3$; $Ag_{0.01}(NH_4)_{0.99}Zr_2(PO_4)_3$; $Ag_{0.05}Na_{0.95}Zr_2(PO_4)_3$; $Ag_{0.2}K_{0.8}Ti_2(PO_4)_3$; $Ag_{0.05}H_{0.05}Na_{0.90}Zr_2(PO_4)_3$; and $Ag_{0.05}H_{0.55}Na_{0.40}Zr_2(PO_4)_3$.

8. The composition of claim 6 wherein antimicrobial compound conforms to $$Na_xH_yAg_zZr_2(PO_4)_3$$

where $x+y+z=1$.

9. An article of manufacture comprising the composition of claim 6.

10. A thermoplastic molding composition characterized by its high transparency comprising aromatic polycarbonate resin and 0.1 to 3.5 weight percent of an antimicrobial compound conforming to formula (I)

$$Ag_aM^1{}_bM^2{}_2(PO_4)_3 \qquad (I)$$

wherein $M^1$ is at least one ion selected from the group consisting of alkali metal ion, alkaline earth metal ion and ammonium ion, $M^2$ is a tetravalent metal selected from the group consisting of Ti, Zr and Sn, a and b are positive numbers and $a+mb=1$ where m is a valence of $M^1$, the percent being relative to the weight of the polycarbonate, said composition including no benzotriazole, said transparency determined as at least 211 lines per inch in accordance with ISO 12233 standard on a flat test specimen 0.1" thick.

* * * * *